United States Patent [19]

Ono

[11] 4,355,906
[45] Oct. 26, 1982

[54] STIRRING APPARATUS FOR CELL CULTURE
[75] Inventor: K. Ray Ono, Bridgeton, N.J.
[73] Assignee: Bellco Glass Inc., Vineland, N.J.
[21] Appl. No.: 250,773
[22] Filed: Apr. 3, 1981
[51] Int. Cl.³ ............................................. B01F 13/08
[52] U.S. Cl. ..................................... 366/274; 366/308
[58] Field of Search ............... 366/247, 274, 273, 279, 366/308

[56] References Cited

U.S. PATENT DOCUMENTS

| | | | |
|---|---|---|---|
| 1,734,120 | 11/1929 | Farrington | 366/308 |
| 2,837,320 | 6/1958 | Baron | 366/274 X |
| 2,859,020 | 11/1958 | Eddy et al. | 366/308 X |
| 3,115,664 | 12/1963 | Del Ponte | 366/247 X |
| 3,572,651 | 3/1971 | Harker | 366/274 X |
| 3,622,129 | 11/1971 | Mazowski | 366/274 X |
| 3,693,941 | 9/1972 | Suchy | 366/274 |

FOREIGN PATENT DOCUMENTS 1326209  3/1963  France .............................. 366/308

Primary Examiner—Philip R. Coe
Assistant Examiner—Christine A. Peterson
Attorney, Agent, or Firm—Seidel, Gonda, Goldhammer & Panitch

[57] ABSTRACT

The apparatus includes a rotatable stirrer assembly for maintaining microcarrier beads in suspension in a cell culture. The stirrer assembly includes at least one blade radially disposed with respect to the vessel axis and connected to the assembly adjacent a magnet member for rotation therewith about said axis.

8 Claims, 10 Drawing Figures

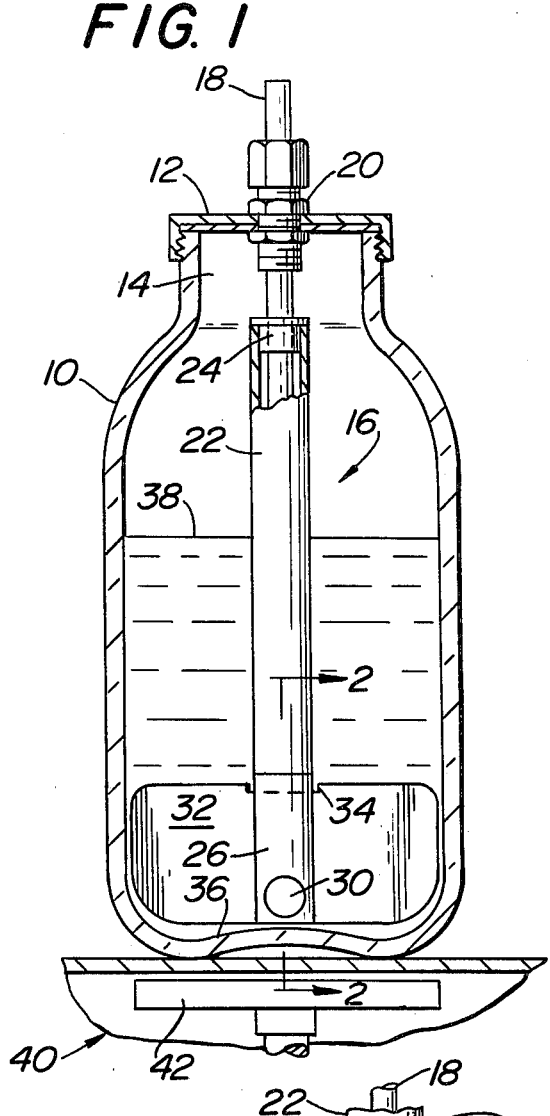
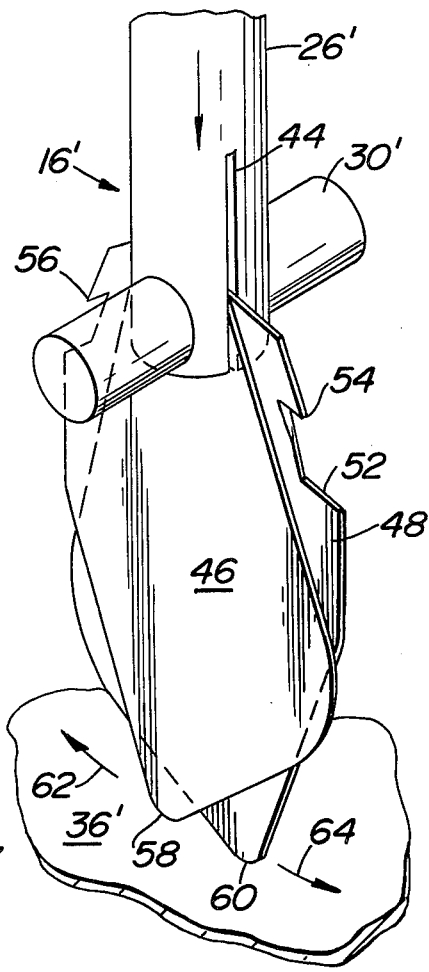
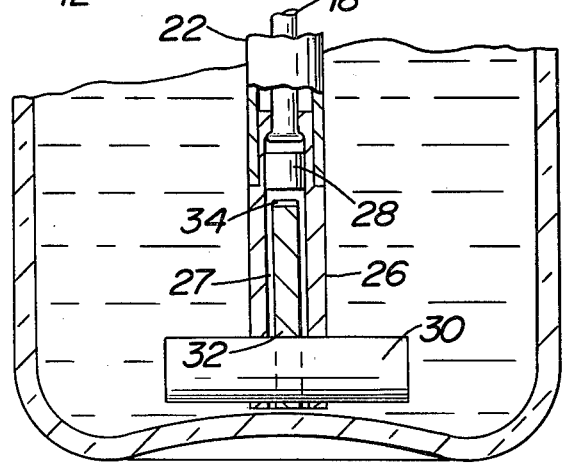
FIG. 1
FIG. 3
FIG. 2

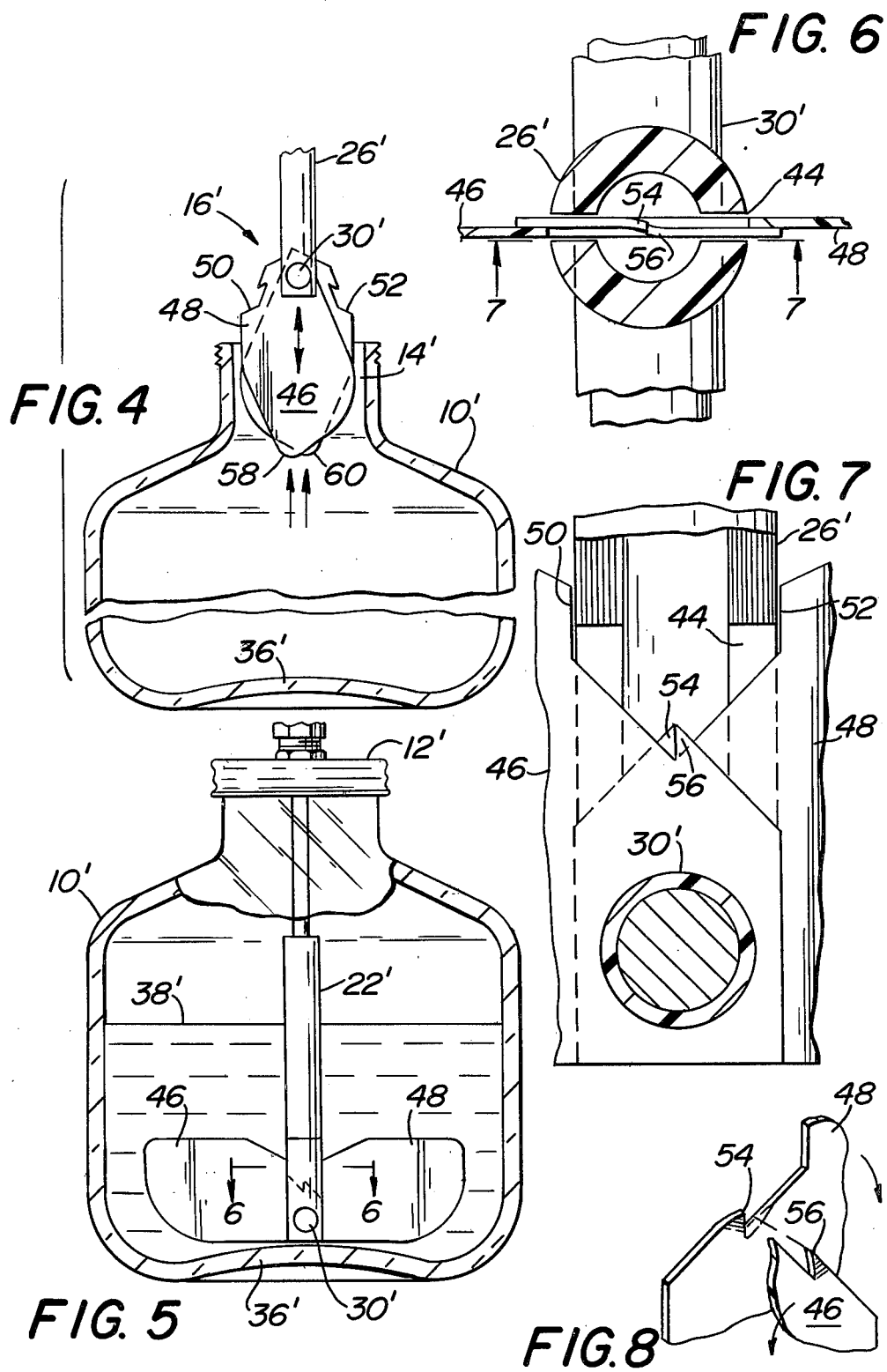

STIRRING APPARATUS FOR CELL CULTURE

BACKGROUND

Microcarrier beads for use in cell culture are known. For example, such beads can be of the type sold commercially under either of the trademarks "CYTODEX-1" or BIOSILON. Microcarrier beads are available in sizes of 50–150 microns and are generally used with a concentration of up to 5 mg/ml. The beads are preferably provided with a charge opposite to that of the cells so that hundreds and hundreds of cells will attach to each bead.

One factor that affects yields is the problem of retaining the cells attached to the beads. The stirring speed causes collision between beads which results in cells being detached from the beads. Even if there are no collisions, cells and beads can become detached due to the fact that not all cells attach to a bead with the same tenacity. Hence, the mere movement of the culture can cause detachment. Once a cell is detached, it will not reattach itself to a bead. It has been recommended heretofore that the stirring speed of a device as disclosed in U.S. Pat. No. 3,622,129 should be very slow, namely 50–150 rpm depending upon vessel design and other factors. With stirring speeds below that speed range, it has been reported that the beads do not remain in suspension in the cell culture and cell growth is poor.

Toward the end of a culture growth cycle, the beads become heavier and heavier due to the build-up of cells which grow at an exponential rate. Hence, it has been necessary heretofore to increase the stirring speed during the cycle to maintain the beads in suspension.

The present invention is directed to a solution to the problem of providing stirring apparatus for maximizing yields in connection with microcarrier bead cell cultures.

SUMMARY OF THE INVENTION

The stirring apparatus for cell culture of the present invention includes a vessel made from a non-magnetic material. A stirrer assembly is provided for stirring the contents of the vessel. The stirrer assembly includes a member capable of being rotated by magnetic forces when the member is adjacent the bottom of the vessel. The stirrer assembly includes at least one blade which is radially disposed with respect to the vessel axis and preferably with upright side faces. The blade is connected to the stirrer assembly adjacent the member responsive to magnetic forces for rotation therewith about said axis.

In one embodiment of the invention, the stirrer assembly includes a single fixed blade. In another embodiment of the invention, the stirrer assembly includes a pair of blades pivotably mounted. The specific embodiment utilized depends upon the size and shape of the vessel. Each stirrer assembly is insertable through an opening in the vessel.

The present invention solves the problem by providing the stirrer assembly with a blade which causes sufficient circulation to maintain the microcarrier bead in suspension while at the same time using a much slower speed than that utilized heretofore such as 5–45 rpm.

It is an object of the present invention to provide novel apparatus for use with microcarrier bead cell cultures which maximizes yields.

It is another object of the present invention to provide a stirrer assembly wherein stirrer blades extend for a radial dimension so as to be close to the inner periphery of the vessel while being capable of being introduced through a narrow inlet opening on the vessel.

It is an object of the present invention to provide stirring apparatus which will maintain microcarrier beads in suspension at a uniform very slow stirring speed during the entire cycle while minimizing detachment between beads and cells.

Other objects and advantages will appear hereinafter.

For the purpose of illustrating the invention, there is shown in the drawings a form which is presently preferred; it being understood, however, that this invention is not limited to the precise arrangements and instrumentalities shown.

FIG. 1 is a vertical sectional view through one embodiment of the present invention.

FIG. 2 is an enlarged detail view taken along the line 2—2 in FIG. 1.

FIG. 3 is a partial perspective view of another embodiment of the present invention.

FIG. 4 is a vertical sectional view of apparatus in accordance with the second embodiment of the present invention and illustrates the stirrer assembly being introduced through the inlet opening of a vessel.

FIG. 5 is a view similar to FIG. 4 but showing the assembly in an operative disposition.

FIG. 6 is a sectional view taken along the line 6—6 in FIG. 5 but on an enlarged scale.

FIG. 7 is a sectional view taken along the line 7—7 in FIG. 6.

FIG. 8 is a partial perspective view of a portion of the blades shown in FIGS. 3-7.

DETAILED DESCRIPTION

Figure 9:
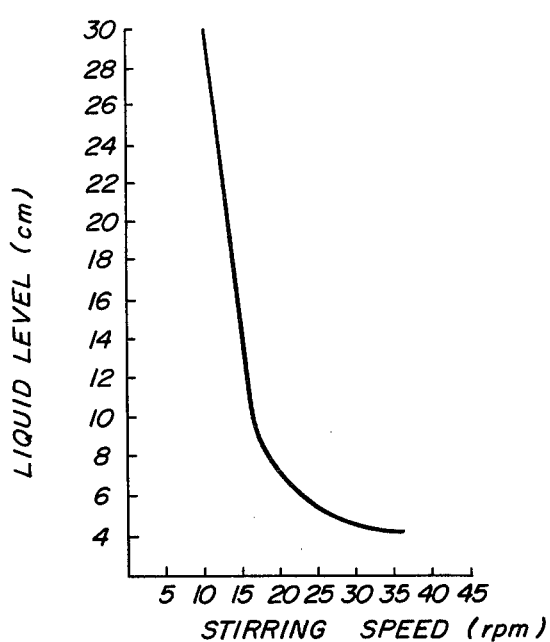
FIG. 9 is a graph showing liquid level versus stirring speed.

Referring to the drawings in detail, wherein like numerals indicate like elements, there is shown in FIG. 1 a vessel designated generally as 10. The vessel 10 is made from a non-magnetic material such as glass, ceramic, etc. The shape of the vessel 10 may vary widely and may include a pouring spout as taught by FIG. 1 of U.S. Pat. No. 3,622,129, may include means for introducing and withdrawing culture, etc. I have found that beads are more easily placed into suspension when vessel 10 has a crowned bottom as shown as opposed to a flat bottom.

The vessel 10 is provided with an inlet opening 14 and a removable cover 12. The cover 12 supports a stirrer assembly 16 mounted on the shaft 18. Shaft 18 may be made from any one of a wide variety of materials capable of being sterilized but preferably is made from glass. Shaft 18 is vertically adjustable with respect to the vessel 12 by the use of lock nuts 20 on opposite sides of the cover 12 and a plastic compression fitting.

The stirrer assembly 16 includes a tube 22 having a length slightly shorter than the height of the vessel 10. Tube 22 is supported at its upper end by a bushing 24 through which the shaft 18 extends. At its lower end, the tube 22 is telescoped over a reduced diameter portion of a holder 26. Holder 26 is hollow and is rendered solid adjacent its reduced diameter portion by way of the plug 28. Tube 22 and holder 26 are preferably made from an inert material capable of being sterilized such as the material sold commercially under the trademark "TEFLON".

The assembly 16 includes a stirrer member 30 which is preferably of conventional construction wherein a magnetic bar is encased within an inner sterilizable material such as the material sold commercially under the trademark "TEFLON". Member 30 extends through a hole in the holder 26 so as to be perpendicular thereto. The size of the hole in member 26 is chosen so that the member 30 can be inserted or removed with strong finger pressure but will not withdraw from the hole during rotation of the assembly 16.

The lower end of member 26 is provided with a slot 27. A blade 32 extends through the slot 27 in member 26. The height of the slot 27 in member 26 is slightly less than the height of the blade 32. A notch 34 is provided at the upper edge of the blade 32 to act as a limit stop. Notch 34 is slightly longer than the diameter of holder 26. Blade 32 has a hole through which member 30 extends. The length of the notch 34 facilitates any temporary misalignment between the hole and blade 32 and the hole in holder 26 during assembly. Thus, it will be noted that the stirrer member 30 performs the added function of coupling the blade 32 to the holder 26 whereby no additional fasteners or coupling means are needed. Blade 32 has a length which is slightly less than the inner diameter of the vessel 10 and is supported by the assembly 16 immediately adjacent the bottom wall 36 of the vessel 10. Assembly 16 is sufficiently long so that the upper end of the tube 22 is above the level of the culture 38. Thus, culture 38 cannot enter into any portion of the assembly 16 whereby it is not necessary to disassemble the components of assembly 16 between cycles for purposes of sterilization.

The vessel 10 is utilized in a conventional manner using microcarrier beads in the culture 38. When the vessel 10 is placed on top of a drive unit 40, rotation of magnet 42 will induce rotation of the stirrer member 30 which in turn will rotate the assembly 16 about the axes of vessel 10 and shaft 18. The blade 32 maintains the microcarrier beads in suspension in the culture 38. As a result of the very low speed, the cells move at a much slower velocity than that recommended heretofore so as to minimize detachment of the cells from the beads. In addition, the speed is sufficient so as to remain uniform during the entire cycle.

The entire assembly is capable of being inserted into the vessel 10 through the inlet opening 14. Where the ratio of diameter of the vessel 10 to the diameter of the inlet opening 14 is small, the blade 32 may be slightly flexed as it is being introduced through the inlet opening 14 or is withdrawn from the vessel 10. Where the diameter of the vessel 10 is substantially larger than the diameter of the inlet opening, in a vessel such as a vessel having a capacity such as 3 liters or more, it is preferred to provide a blade comprised of two blade members in accordance with a second embodiment of the present invention.

In FIGS. 3-8, there is illustrated another embodiment of the present invention which is identical to that described above except for details of the stirrer assembly and the size of the vessel. Corresponding elements are provided with corresponding primed numerals. As shown more clearly in FIG. 3, the slot at the lower end of the holder 26' is designated 44. A blade is mounted within the slot 44 and is comprised of a pair of blade members designated 46, 48. The blade members 46, 48 each have a hole through which the stirrer member 30' extends whereby the blade members may pivot about the stirrer member 30' from a position as shown in FIG. 3 to a position as shown in FIG. 5.

Blade member 46 has a limit stop 50 and blade member 48 has a limit stop 52. The limit stops cooperate with the holder 26' when the blade members 46, 48 are in the position as shown in FIG. 5. Additional details of this relationship on a larger scale are shown in FIG. 7. It will be noted that the limit stops 50, 52 extend to a position above the upper end of the slot 44.

As shown more clearly in FIGS. 3, 7 and 8, the blade member 48 has a detent 54 while the blade 46 has a detent 56. The detents are preferably in the form of a sharp jagged edge which will overlap one another within the slot 44 as shown in FIG. 7 when the blade members 46, 48 are in their operative position as shown in FIG. 5. Other types of detents may be utilized.

The pivotable mounting for the blade members 46, 48 facilitates an inoperative position for the blade members as shown in FIGS. 3 and 4 when the assembly 16' is being inserted through the inlet opening 14'. The blade tips 58, 60 are tapered and are spaced from one another as shown more clearly in FIGS. 3 and 4 when the assembly 16' is inserted into the vessel 10'. When the tips 58, 60 contact the bottom wall 36' of the vessel 10', continued downward movement of the assembly 16' causes the blade members 46, 48 to pivot about the longitudinal axis of stirrer member 30'. Thus, blade member 46 pivots in the direction of arrow 62 while blade member 48 pivots in an opposite direction as indicted by the arrow 64. The blade members 46, 48 continue to pivot until their limit stops contact the outer peripheral surface of the holder 26' at which time the detents 54, 56 will overlap and lock as shown in FIG. 6. Thereafter, the assembly 16' is elevated so that the bottom edges of the blade members are spaced from but adjacent to the bottom wall 36' as shown in FIG. 5. Assembly 16' is then secured to cover 12' by a lock nut as described above.

When it is desired to remove the assembly 16', the assembly is pulled upwardly. The outer ends of the blade members 46, 48 contact the walls of the vessel 10' adjacent the inlet opening 14'. Such contact disengages the detents 54, 56 whereby the blade members pivot to the position shown in FIG. 4. It will be noted that the height of blade members 46, 48 is slightly less than the diameter of the inlet opening 14'.

The stirrer assembly 16 is usable with only a limited range of vessels. The stirrer assembly 16' can be used with a substantially large number of vessels. The assemblies 16' will differ from one another only in the length and/or height of the blade members 46, 48 so that the outer periphery of the blade members is close to the inner periphery of the vessel vertical walls. The preferred height of the liquid level and the associated stirring speed is shown in FIG. 9. It will be noted that as the height of liquid level increases, the stirring speed necessary to maintain microcarrier beads in suspension decreases.

Figure 10:
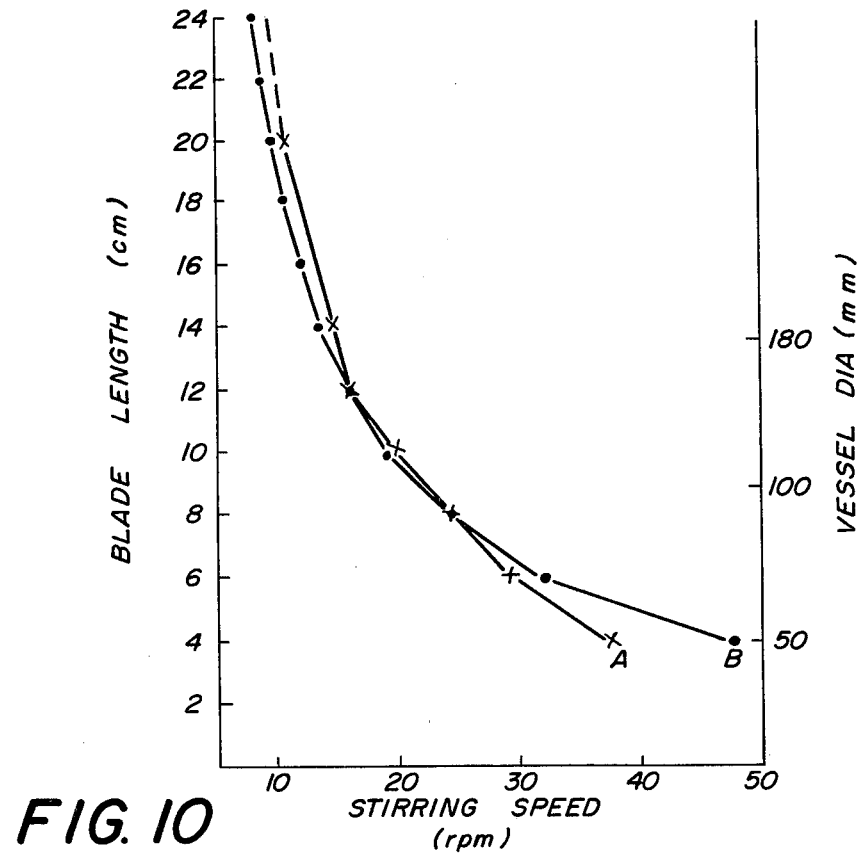
FIG. 10 is a graph showing vessel size and blade length versus stirring speed.

In FIG. 10, curves representing vessel diameter in mm and blade length in cm are plotted versus stirring speed. Curve A is based on visual observation. Curve B is based on computations using the formula, blade tip velocity (cm/sec) equals RPM×blade tip circumference (cm). Blade length is the diameter of the circle defined by the blade tip circumference. Note that curves A and B substantially coincide.

As shown by the curves of FIG. 10, not all vessels should have blades rotating at the same speed. The size of the vessel diameter dictates the stirring speed. Relating stirring speed of vessel diameter is believed to be a departure from prior practices which ignored vessel diameter since such prior practices did not include blades for the purposes used herein. Such vessel diameter is a known factor, FIG. 10 facilitates choosing the preferred blade length and stirring speed.

It is recommended that the vessels be siliconized or otherwise treated prior to use with microcarrier beads. This process involves minimizing the tendency for the microcarrier beads to adhere to the inner peripheral surface of the vessel. Fluids such as dimethyldichlorosilane in an organic solvent are commercially available for this purpose. All components of each embodiment are designed so as to permit sterilization by autoclaving. If desired, the stirrer assembly need not be constructed in a manner whereby tube 22 and holder 26 are separate discrete parts but instead could be integral in one piece. While the blades preferably have upright side faces, the blades may have a pitch if desired.

The present invention makes possible reducing the stirring speed as the size of the vessel increases. Notwithstanding the slower stirring speed for larger size vessels, the microcarrier beads are maintained in suspension but due to their low velocity there is minimal collision contact which could cause detachment of the cells from the beads whereby yield is maximized.

The present invention may be embodied in other specific forms without departing from the spirit or essential attributes thereof and, accordingly, reference should be made to the appended claims, rather than to the foregoing specification, as indicating the scope of the invention.

I claim:

1. Apparatus for use in cell culture comprising a vessel of non-magnetic material, said vessel having an inlet opening whose diameter is less than the diameter of the vessel, a stirring assembly insertable into the vessel through said opening for stirring the contents of the vessel, said assembly including a stirring member for rotating the assembly in response to magnetic forces, said assembly including an elongated holder having a slot at its lower end, first and second blades in said slot, said blades having a combined length which is greater than the diameter of said opening, said stirring member extending through a hole in said blades, said blades being mounted for pivotable movement downwardly about the longitudinal axis of said stirring member, said stirring member being generally perpendicular to said axis of said holder and being encapsulated in an inert sterilizable material.

2. Apparatus in accordance with claim 1 wherein said blades overlap one another in said slot, detent means for latching said blades in a position radially disposed to the longitudinal axis of said holder.

3. Apparatus in accordance with claim 1 wherein the inner surface of the bottom wall of said vessel is convex, said stirring member being positioned adjacent said bottom wall.

4. Apparatus in accordance with claim 1 wherein the lower half of said holder is cylindrical and of uniform diameter.

5. A method of causing microcarrier beads to remain in suspension in a cell culture within a vessel whose diameter exceeds the diameter of an inlet opening on the vessel comprising the steps of inserting a stirring assembly through the inlet opening with the assembly having a blade whose length is greater than the diameter of said inlet opening, pivoting two portions of said blade from an inoperative position to an operative position about the axis of a magnetic stirring member while disposed in said vessel by contacting said blade portions with the bottom wall of the vessel, using magnetic forces to rotate the assembly at a speed of about 5 to 45 RPM while the blade stirs the cell culture to maintain the microcarrier beads in suspension.

6. A method in accordance with claim 5 including using the blade whose length is correlated to the desired speed in said range substantially as shown in FIG. 10.

7. A method in accordance with claim 5 including using a vessel whose bottom wall is convex on the inner surface of the vessel.

8. A method in accordance with claim 5 including causing said blade portions to latch in their operative position wherein they are radially disposed with respect to the axis of rotation of said assembly.

* * * * *